US00PP08990P

United States Patent [19]

Sherrill

[11] Patent Number: Plant 8,990

[45] Date of Patent: Nov. 29, 1994

[54] SHERRILL DELIGHT PEACH TREE

[76] Inventor: Lewis B. Sherrill, 3265 Valpredo Rd., Arvin, Calif. 93203

[21] Appl. No.: 210,602

[22] Filed: Mar. 17, 1994

[51] Int. Cl.[5] ..... A01H 5/00

[52] U.S. Cl. ..... Plt./43.1

[58] Field of Search ..... Plt. 43.1

*Primary Examiner*—James R. Feyrer

*Attorney, Agent, or Firm*—Worrel & Worrel

[57] ABSTRACT

A new and distinct variety of peach tree which is somewhat remotely similar to the "Goldcrest" peach tree (Unpatented) and the "Queencrest" peach tree (U.S. Plant Pat. No. 6,025), but from which it is distinguished by producing a more highly colored fruit which are mature for commercial harvesting and shipment approximately May 1 through May 5 in the San Joaquin Valley of central California, or about three or four days after the "Goldcrest" peach tree and approximately two to three days ahead of the "Queencrest" peach tree.

1 Drawing Sheet

BACKGROUND OF THE NEW VARIETY

The present invention relates to a new and distinct variety of peach tree which will hereinafter be denominated varietally as "Sherrill Delight" and, more particularly, to a peach tree which produces clingstone fruit which are mature for commercial harvesting and shipment approximately May 1 through May 5 in the San Joaquin Valley of central California and which are highly colored and of good quality.

The discovery and development of new varieties of early ripening fruit trees in an endeavor of potentially considerable commercial significance. This potential is, however, frequently unrealized due to the multifarious criteria by which new varieties may be judged and the unlikely possibility that any single new variety will possess sufficient merit relative thereto to become successful commercially.

Two commercially successful, early ripening peach trees are the "Goldcrest" peach tree (Unpatented) and the "Queencrest" peach tree (U.S. Plant Pat. No. 6,025) which ripen respectively in late Apr. and early May in the San Joaquin Valley of central California. The variety of the present invention is a promising candidate for commercial success in that it bears fruit ripening between these two known varieties and possessing very good flavor while having a superior, more intense skin coloration.

ORIGIN AND ASEXUAL REPRODUCTION OF THE NEW VARIETY

The present variety of peach tree hereof was discovered by the inventor as a chance seedling grown from early varieties which were growing in an experimental orchard located in Arvin in the San Joaquin Valley of central California. Various seedlings began to grow in 1985. In 1989, trees of the new variety were asexually reproduced by budding to the subject variety in a test plot. The first fruit from the budded trees was observed in 1991 and 1992. The inventor has continued to observe the asexually reproduced trees and has confirmed that they are identical in all respects to the parent tree.

SUMMARY OF THE NEW VARIETY

The "Sherrill Delight" peach tree is characterized by producing a clingstone fruit which has red skin coloration and is ripe for commercial harvesting and shipment approximately May 1 through May 5 in the San Joaquin Valley of central California. The new variety can be compared with the "Goldcrest" peach tree (Unpatented) and the "Queencrest" peach tree (U.S. Plant Pat. No. 6,025), but is distinguishable therefrom by the aforementioned ripening date and superior fruit coloration. The new variety ripens approximately three to four days after the "Goldcrest" peach tree and approximately two to three days ahead of the "Queencrest" peach tree. With regard to fruit shape, the new variety is intermediate in shape between the "Goldcrest" peach and the "Queencrest" peach. The new variety is ovate in shape, substantially less elongated and pointed than the "Goldcrest" peach, but not quite as globose in form as the "Queencrest" peach. The fruit is clingstone having a sweet flavor and red blush skin coloration.

BRIEF DESCRIPTION OF THE DRAWING

The accompanying drawing is a color photograph showing fruit of the new variety including a first showing the base end; a second in side elevation showing the suture thereof; a third showing the apex end; a fourth sectioned to show the flesh thereof; a fifth in side elevation; and foliage typical of the new variety of peach tree.

DETAILED DESCRIPTION

Referring more specifically to the pomological details of this new and distinct variety of peach tree, the following has been observed under the ecological conditions prevailing at the orchard of origin which is located in Arvin, Calif. All major color code designations are by reference to the *Dictionary of Color*, by Maerz and Paul, First Edition, 1930. Common color names are also occasionally employed.

TREE

Generally: Tree is hardy as grown under climatic conditions typical for the southern San Joaquin Valley of California. Upright shoots of one to two feet develop regularly during the early growing season, but are removed regularly prior to full extension.

Size: Trees have been trained in a modified central leader form and are kept reduced in size by frequent summer pruning to facilitate harvest without the use of ladders.

Vigor: Vigorous.

Form: Upright to upright-spreading.
Productivity: Productive.
Regularity of bearing: Regular.
Trunk:
*Size.*—Medium thickness.
*Surface texture.*—Moderately rough.
*Color.*—Dark gray (8-C-7).
*Lenticels — size.*—Average.
*Lenticels — size — length.*—5 mm (0.1968 inches) to 11 mm (0.4331 inches).
*Lenticels — size — height.*—2 mm (0.0787 inches) to 3 mm (0.1181 inches).
*Lenticels — shape.*—Oval, flattened longitudinally.
Branches:
*Size.*—Medium thickness.
*Surface texture.*—Relatively smooth.
*Color — one year or older wood.*—Medium brown (7-J-11 Cordova Brown).
*Color — immature branches.*—Light green (19-K-6 Sea Green) with new expanding shoot tips a light yellow-green (17-L-3 Endive Green).
*Fruiting hanger wood.*—Internode length — 14 mm (0.5512 inches) to 26 mm (1.0236 inches).

LEAVES

Size:
*Generally.*—Medium to large. Leaf measurements were taken from leaves growing on vigorous, upright shoots of current season's growth.
*Average length.*—16.8 cm (6.6142 inches) to 18.3 cm (7.2047 inches), including the petiole.
*Average width.*—3.6 cm (1.4173 inches) to 4.3 cm (1.6929 inches).
Thickness: Average.
Form: Lanceolate. The leaf apex is acuminate.
Color:
*Upwardly disposed surface.*—Dark green (24-L-3).
*Downwardly disposed surface.*—Lighter grey-green (22-J-4).
Marginal form:
*Generally.*—Crenate, with large, broad, low, regular crenations.
Leaf margin: Slightly undulate.
Glandular characteristics: The leaf glands are relatively large in size and reniform in type. From 1 to 4 glands are usually present, located on the very base of the lower leaf margin. Occasionally, 1 or 2 of these glands can be present upon the petiole itself at the juncture of the petiole and lower leaf margin. Gland position is variable. Most frequently the glands are in an alternate position, but occasionally opposite pairs can be found.
Glands:
*Color.*—Bright yellow-green (19-L-4).
Petiole:
*Size.*—Medium.
*Length.*—7 mm (0.2756 inches) to 10 mm (0.3937 inches).
*Thickness.*—1.5 mm (0.0590 inches) to 2 mm (0.0787 inches).
*Color.*—Light green (18-L-7), slightly darker within the petiole groove.
Stipules: Early deciduous.
*Size.*—Medium to large.
*Length, fully expanded.*—12 mm (0.4724 inches) to 15 mm (0.5905 inches).
*Form.*—Narrow linear lanceolate with serrate margins.
*Color.*—Light green (19-L-5 Cosse Green) with occasional reddish tones present.

FLOWERS

Flower buds:
*Generally.*—Buds are relatively free from the bearing shoot. Bud scale surfaces are pubescent. The floral buds are hardy under climatic conditions typical for the southern San Joaquin Valley of California.
*Size.*—Medium.
*Color.*—Medium grey (7-C-8) with patches of brown color in varying shades.
*Form.*—Conic.
Flowers:
*Generally.*—Medium to large in size and of the "showy" type.
*Date of bloom.*—Mar. 3, 1993. Average or about mid-season in relation to other peach cultivars growing in the region.
*Bloom quantity.*—Abundant with one to three floral buds present per node.
*size.*—Diameter — Fully expanded, ranges from 37 mm (1.4567 inches) to 42 mm (1.6535 inches).
Petals:
*Size.*—Medium to large.
*Length.*—18 mm (0.7087 inches) to 22 mm (0.8661 inches).
*Width.*—14 mm (0.5512 inches) to 16 mm (0.6299 inches).
*Number.*—Five.
*Form.*—Ovate.
*Color.*—When young, a light pink (1-D-1) with a slightly darker coloration (1-F-3) basally and on the petal claw. The petals darken in color with age to a rose color (1-F-4 France Rose), especially in the basal area.
*Claw — size.*—Medium, average 1.5 mm (0.0590 inches) in width and 2 mm (0.0787 inches) in length.
*Claw — form.*—Truncate.
*Margin.*—Quite undulate both apically and laterally.
*Apex.*—Moderately raised and rounded.
Pedicel:
*Length.*—Short, from 1.5 mm (0.0590 inches) to 2.0 mm (0.0787 inches).
*Thickness.*—Average 1.5 mm (0.0590 inches).
*Color.*—Medium green (18-J-5).
*Surface.*—Glabrous.
Calyx:
*Surface.*—Glabrous.
*Color.*—Maroon (7-E-1 Canyon).
Sepals:
*Size.*—Medium.
Form.—Ovate.
*Surface.*—Pubescent with moderately long greyish hairs.
*Color.*—Maroon (7-E-5 Mauverose).
Nectaries:
*Color.*—Dull orange (12-B-12 Eldorado), becoming slightly darker and more dull with age.
Anthers:
*Size.*—Average.
*Color.*—Bright red (5-K-11 Maroccan Red) dorsally and buff colored (11-H-3) ventrally. Pollen is abundant and is of a yellow-gold (9-L-4 Sunflower) coloration.

Stamens:

*Length.*—Longer in length than the pistil at full development. 15 mm (0.5905 inches) to 19 mm (0.7480 inches).

Filament:

*Color.*—Light pink (1-A-2) when young, becoming a dark rose (2-E-4) with maturity.

Pistil:

*Length.*—Ranges from 16 mm (0.6299 inches) to 17 mm (0.6693 inches) including the ovary.

*Color.*—Very pale green (18-C-2) when young, becoming tinged with red with advancing maturity.

*Surface.*—Very pubescent.

FRUIT

Maturity when described: Ripe for commercial harvesting and shipment approximately May 1 to May b 5 in 1993 near Arvin in the southern San Joaquin Valley of California.

Size:

*Generally.*—Large for its early date of maturity. Uniform.

*Average diameter in the cheek plane.*—62 mm (2.441 inches) to 70 mm (2.756 inches).

*Average diameter in the axial plane.*—64 mm (2.520 inches) to 66 mm (2.598 inches).

*Average diameter in the suture plane.*—60 mm (2.362 inches) to 65 mm (2.559 inches).

Form:

*Uniformity.*—Ovate in form in lateral aspect. The fruit is variable in apical aspect, from oval to nearly globose in form.

*Symmetry.*—Most frequently the fruit is asymmetrical with one side slightly larger than the other.

Suture:

*Generally.*—The suture is a thin, slightly indented line extending from base to apex. The suture line is more noticeable over the apical shoulder of the ventral surface. The suture is slightly folded within the cavity basin. A slight amount of stitching is apparent along the suture line, most commonly found near mid-suture. The suture is usually not striped, but takes on the color of the surrounding area.

Ventral surface:

*Generally.*—Relatively smooth with only slight lipping, usually stronger on one half of the fruit.

Stem cavity:

*Size.*—Medium.

*Width.*—22 mm (0.8661 inches) to 26 mm (1.024 inches).

*Depth.*—10 mm (0.3937 inches) to 12 mm (0.4724 inches).

*Length.*—26 mm (1.024 inches) to 31 mm (1.220 inches).

*Shape.*—Oval and relatively shallow. The cavity shoulder is frequently slightly indented where the fruit was pressed next to the bearing limb.

Stem:

*Length.*—Short, 7 mm (0.2756 inches) to 9 mm (0.3543 inches).

*Thickness.*—3 mm (0.1181 inches) to 3.5 mm (0.1378 inches).

*Color.*—Light olive green (21-L-4) with occasional streaks of brown.

Base:

*Form.*—Variable from generally rounded to slightly truncate. The base angle is usually very slightly oblique to the fruit axis.

Apex:

*Shape.*—Moderately pointed. A distinct depression is present on the ventral suture side of the apex.

Pistil point:

*Position.*—Variable, but most often very slightly oblique.

Skin:

*Thickness.*—Average.

*Texture.*—Pubescent with relatively sparse, short, greyish pubescence. Skin flavor is slightly acidic and slightly astrigent. The skin is tenacious to the flesh at commercial maturity.

*Tendency to crack.*—None observed.

*Color.*—The skin surface is highly colored, from 90 to 100 percent red blushed.

*Blush color.*—Composed of an underlying bright red washed coloration (4-L-12 Buccaneer Red), overlain with a darker garnet red dappling (7-L-4 Akbar Red). This darker red color is also often present over the apex and adjacent areas. Only a small percentage of yellow ground color is present (0 to 10 percent) and is usually found basally or on the basal shoulders where the fruit was pressed next to the bearing limb.

*Ground color.*—Yellow-gold (10-K-6 Chinese Yellow).

Flesh:

*Flesh color.*—Medium yellow (10-K-5), occassionally with a greenish tinge near the pit cavity. A slight amount of red flecking can be present in the flesh just under the skin surface. This flecking becomes more pronounced with advanced maturity.

*Flavor.*—Sweet with moderate acidity. The flavor is very good for its early season of maturity.

*Aroma.*—Slight and pleasant.

*Texture.*—The flesh is very firm and crunchy at commercial maturity with slightly coarse texture.

*Fibers.*—Numerous relatively long, light-colored fibers are present throughout the flesh.

*Ripening.*—Evenly.

*Eating quality.*—Very good.

Stone:

*Attachment.*—Full clingstone. Tightly attached to the flesh at commercial maturity.

*Fibers.*—Numbers — Numerous medium length fibers are firmly attached to the stone throughout its surface.

*Size.*—Medium.

*Size — length.*—Ranges from 28 mm (1.102 inches) to 32 mm (1.260 inches).

*Size — width.*—22 mm (0.8661 inches) to 26 mm (1.024 inches).

*Size — Thickness.*—17 mm (0.6693 inches) to 20 mm (0.7874 inches).

*Form.*—Generally — Ovate. The stone is very soft at commercial maturity.

*Apex.*—Shape — Pointed with an acute tip.

*Color.*—Dry — Chamois-tan (11-E-5 Raffia).

*Base.*—Shape — Iregular, but most frequently rounded. The base is oblique to the stone axis.

*Sides.*—Generally — Variable, but most frequently unequal.

*Surface.*—Rather coarse laterally with large ridges, especially over the apical shoulders. Sides are heavily pitted from mid-stone to the base laterally.

*Hilum.*—Medium in size, roughly oval in form and heavily eroded.

*Ventral edge.*—Relatively narrow, from 3 mm (0.1181 inches) to 4 mm (0.1575 inches) in thickness at mid-suture and usually with a relatively strong wing, especially basally on the ventral suture.

*Dorsal edge.*—Relatively narrow, from 3.5 mm (0.1378 inches) to 4.5 mm (0.1772 inches) at mid-stone. A moderately narrow groove is present along the dorsal edge, from the stone base to about mid-stone. Above mid-stone the groove narrows and the suture is moderately eroded.

*Tendency to split.*—Numerous stones are split internally, but only a few are visible externally.

Although the new variety of peach tree possesses the described characteristics noted above as a result of the growing conditions prevailing near Arvin, Calif. in The San Joaquin Valley of California, it is to be understood that variations of the usual magnitude and characteristics incident to changes in growing conditions, irrigation, fertilization, pruning, pest control, climatic variation and the like are to be expected.

Having thus described and illustrated my new variety of peach tree, what I claim as new and desire to be secured by Plant Letters Patent is:

1. A new and distinct variety of peach tree substantially as illustrated and described which is somewhat remotely similar to the "Goldcrest" peach tree (Unpatented) and the "Queencrest" peach tree (U.S. Plant Pat. No. 6,025), but from which it is distinguished by producing a more highly colored fruit which are mature for commercial harvesting and shipment approximately May 1 through May 5 in the San Joaquin Valley of central California, or about three or four days after the "Goldcrest" peach tree and approximately two to three days ahead of the "Queencrest" peach tree.

* * * * *

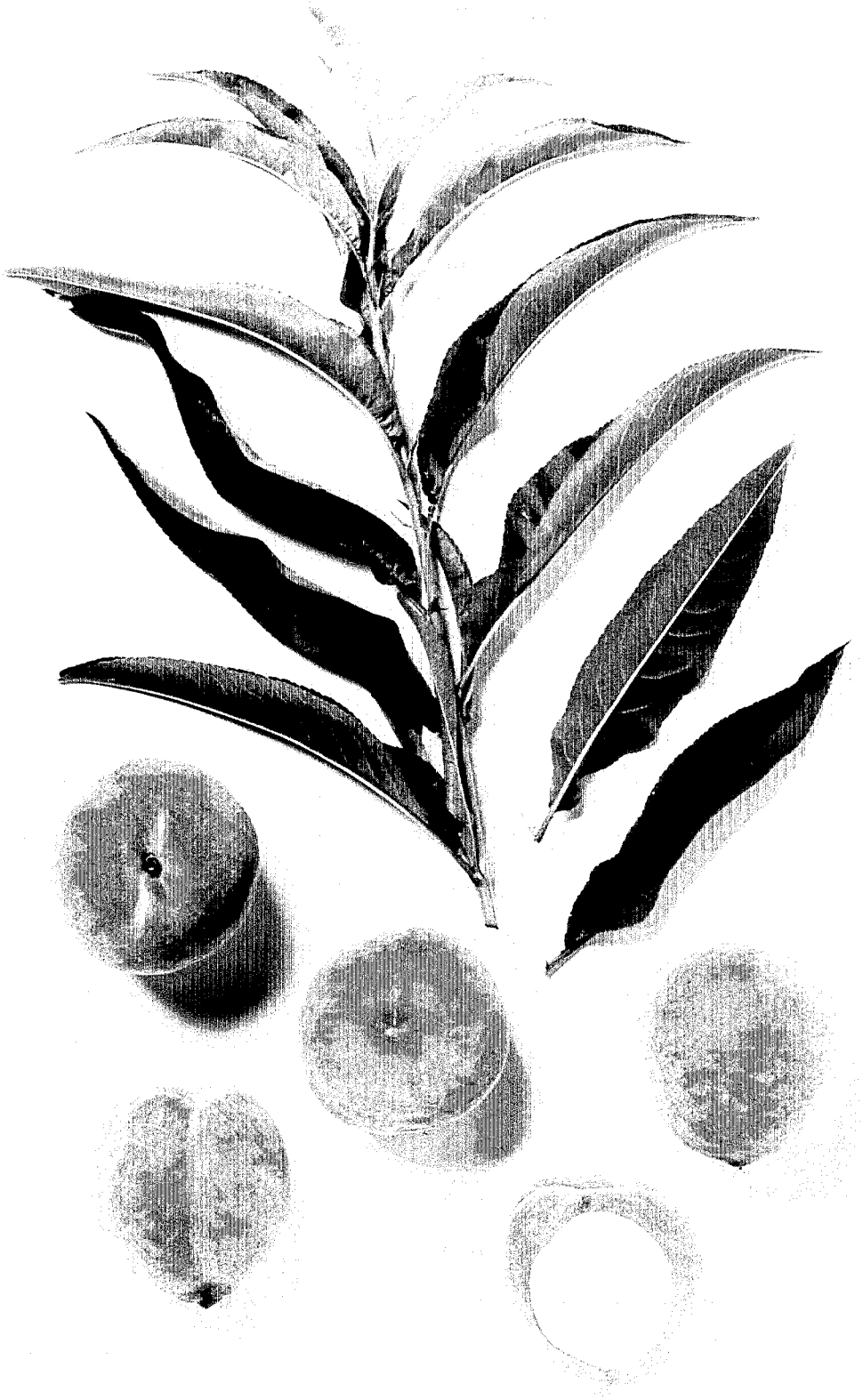

UNITED STATES PATENT AND TRADEMARK OFFICE

CERTIFICATE OF CORRECTION

PATENT NO. : PP: 8,990

DATED : NOVEMBER 29, 1994

INVENTOR(S) : LEWIS B. SHERRILL

It is certified that error appears in the above-identified patent and that said Letters Patent is hereby corrected as shown below:

Column 4, line 65, delete "Maroccan" and substitute ---Moroccan---.

Column 5, line 18, delete the "b" between May and 5.

Column 6, line 14, delete "astrigent" and substitute ---astringent---.

Column 6, line 65, delete "Iregular" and substitute ---Irregular---.

Signed and Sealed this

Fourth Day of April, 1995

*Attest:*

*Attesting Officer*

BRUCE LEHMAN

*Commissioner of Patents and Trademarks*